(12) United States Patent
Schwager et al.

(10) Patent No.: US 8,603,035 B2
(45) Date of Patent: Dec. 10, 2013

(54) CATHETER

(75) Inventors: Michael Schwager, Winterthur (CH);
Rolf Vogel, Boll-Sinneringen (CH)

(73) Assignee: Schwager Medica AG, Winterthur (CH)

( * ) Notice: Subject to any disclaimer, the term of this patent is extended or adjusted under 35 U.S.C. 154(b) by 0 days.

(21) Appl. No.: 13/203,496

(22) PCT Filed: Feb. 17, 2010

(86) PCT No.: PCT/CH2010/000041
§ 371 (c)(1),
(2), (4) Date: Nov. 10, 2011

(87) PCT Pub. No.: WO2010/096940
PCT Pub. Date: Sep. 2, 2010

(65) Prior Publication Data
US 2012/0046646 A1 Feb. 23, 2012

(30) Foreign Application Priority Data
Feb. 27, 2009 (CH) .......................................... 295/09

(51) Int. Cl.
*A61M 5/178* (2006.01)

(52) U.S. Cl.
USPC .................. 604/160; 604/164.13; 604/164.01

(58) Field of Classification Search
USPC .......... 604/158, 160, 164.01, 164.05, 164.09, 604/164.13, 523, 528–529
See application file for complete search history.

(56) References Cited

U.S. PATENT DOCUMENTS

| | | | | |
|---|---|---|---|---|
| 5,389,087 A | * | 2/1995 | Miraki | 604/247 |
| 6,273,879 B1 | * | 8/2001 | Keith et al. | 604/523 |
| 7,074,231 B2 | * | 7/2006 | Jang | 606/194 |
| 7,867,271 B2 | * | 1/2011 | Geiser et al. | 623/1.12 |
| 8,088,103 B2 | * | 1/2012 | Teeslink et al. | 604/101.03 |

FOREIGN PATENT DOCUMENTS

| | | |
|---|---|---|
| WO | WO 93/05841 A1 | 4/1993 |
| WO | WO 00/69499 A1 | 11/2000 |

* cited by examiner

*Primary Examiner* — Nicholas Lucchesi
*Assistant Examiner* — Rebecca E Eisenberg
(74) *Attorney, Agent, or Firm* — Birch, Stewart, Kolasch & Birch, LLP

(57) ABSTRACT

A catheter (100, 200) for insertion into a human and/or animal hollow organ, comprising a catheter shaft (110, 210) with a lumen (120, 220), which opens into a front opening at a distal end (112, 212) of the catheter shaft (110, 210), wherein the catheter shaft (110, 210) has at least a first lateral opening (130, 230a) that is at a distance from the distal end (112, 212) and opens into the lumen (120, 220), is distinguished by virtue of the fact that there is at least a first insertion device (140, 240a), arranged on an external side (114, 214) of the catheter shaft (110, 210) in a region of the first lateral opening (130, 230a), for a wire-like element (300, 400, 500) that should be inserted into the first lateral opening (130, 230a) from the outside.

20 Claims, 5 Drawing Sheets

CATHETER

TECHNICAL FIELD

The invention relates to a catheter for insertion into a human and/or animal hollow organ, comprising a catheter shaft with a lumen, which opens into a front opening at a distal end of the catheter shaft, wherein the catheter shaft has at least a first lateral opening that is at a distance from the distal end and opens into the lumen.

PRIOR ART

Catheters usually are tubules and/or tubes of varying diameters, for example made of plastic, latex, silicone, metal, or glass. They can be used to probe, penetrate, empty, fill, and/or rinse hollow organs such as e.g. the urethra, esophagus, stomach, intestines, bile ducts, vessels, and/or blood-conducting arteries, such as e.g. cardiac arteries, of humans and/or animals. In particular, this occurs for diagnostic and/or therapeutic reasons.

In particular, catheters can also be used to introduce into hollow organs interventional and/or diagnostic elements in particular, more particularly in the form of wire-like elements, e.g. special probe wires for diagnostic purposes. In the process, the catheter acts as a guide for e.g. a wire-like element that cannot be introduced directly into the hollow organ as a result of its mechanical properties.

To this end, so-called monorail catheters are often used in practice, which are based on the rapid exchange system. Such catheters are introduced into the hollow organ following a guide wire that was previously introduced into the hollow organ. In contrast to catheters in which the guide wire is routed centrally through the entire catheter (according to the conventional "over-the-wire system"), the guide wire in a monorail catheter merely runs through the catheter in a distal region between the catheter tip and a lateral opening at a distance from the catheter tip. A monorail catheter can particularly advantageously be withdrawn from the hollow organ (and, if need be, be pushed back therein), wherein the guide wire can remain in the hollow organ without having to attach an extension wire to the guide wire. This greatly simplifies handling.

When the distal end or catheter tip of the monorail catheter has been placed at the desired point in the hollow organ, the guide wire can be withdrawn such that it emerges from the catheter through the lateral opening and the wire-like element can from the proximal end be introduced into the hollow organ through a central lumen in the catheter. The corresponding diagnostic and/or therapeutic treatment can subsequently be undertaken.

In principle, it would be advantageous in various applications if the monorail catheter were completely withdrawn from the hollow organ after the wire-like element was positioned such that merely the wire-like element remains in the hollow organ. This is because if the monorail catheter is inserted into the hollow organ through e.g. a fixed coronary catheter, said monorail catheter massively reduces the free cross section of the coronary catheter, which, for example, makes it much harder to introduce fluids through the coronary catheter. The presence of the monorail catheter particularly hinders the introduction of highly viscous contrast agents, which for example have to be introduced into the hollow organ for intravascular imaging (e.g. in optical coherence tomography).

In principle, of course, there is the option of designing the probe wire with a corresponding greater length such that the monorail catheter can be completely withdrawn. However, this is disadvantageous for economic reasons and, moreover, the longer wire-like elements in practice make handling more complex. Attaching extension pieces, as done for guide wires, is generally not possible in the case of probe wires. This is because probe wires generally have a large-volume connection piece at the proximal end, which renders impossible a withdrawal of the catheter.

Thus, there still is the need for an improved catheter, which more particularly simplifies the introduction of interventional and/or diagnostic elements, more particularly in the shape of wire-like elements, into human and/or animal hollow organs.

DESCRIPTION OF THE INVENTION

It is an object of the invention to develop a catheter that belongs to the technical field specified at the outset, can be used in a more flexible fashion, and more particularly allows more efficient procedures when using wire-like elements in human and/or animal hollow organs for diagnostic, therapeutic, and/or surgical purposes.

The solution to the object is defined by the features of claim 1. According to the invention, there is at least a first insertion device, arranged on an external side of the catheter shaft in a region of the first lateral opening, for a wire-like element that should be inserted into the first lateral opening from the outside.

The catheter shaft is preferably embodied as a flexible tubule and/or as a tube. The catheter shaft advantageously has a substantially circular cross section. Such catheter shafts can be inserted particularly well into hollow organs. However, in principle, other cross sections, e.g. oval or polygonal cross sections, are also feasible.

More particularly, the distal end of the catheter shaft here is understood to mean the end of the catheter shaft that should be inserted into the hollow organ. In other words, the catheter is inserted into the hollow organ with a leading distal end. Accordingly, the proximal end of the catheter shaft more particularly is the end of the catheter shaft facing away from the hollow organ. Thus, the proximal end of the catheter shaft is not usually inserted into the hollow organ.

In this context, the term lumen more particularly means an internal cavity of the catheter shaft that, in particular, completely runs through the catheter shaft from the proximal end to the distal end. More particularly, the lumen is a passable, substantially cylindrical cavity, wherein the latter can in sections also have a non-cylindrical, tapered, and/or dilated design. However, in principle, provision can also be made for a lumen that does not extend through the entire catheter shaft and e.g. emerges from the catheter shaft in a region in front of the proximal end.

A material of the catheter shaft advantageously consists of a plastic, at least in a distal section. Plastics firstly are sufficiently flexible and can moreover often be processed in a relatively simple fashion. The catheter shaft is advantageously completely formed from a plastic. However, a proximal section of the catheter shaft in particular may also consist of a metallic and/or another material. However, it is also possible to use other materials for the catheter shaft in place of plastic, or in addition thereto.

In this context, a wire-like element is particularly understood to mean a flexible body, the length of which is many times larger, preferably at least by a factor of 100, than its diameter and/or its width. The wire-like element can more particularly have a circular cross section and need not be metallic. More particularly, the wire-like element is a special wire and/or a probe wire for a diagnostic method, and e.g.

contains fiber optics. The wire-like element advantageously is a probe wire for optical coherence tomography. In this case a measurement head in particular is arranged at a distal end of the wire-like element. However, the wire-like element can also be a conventional guide wire, for example, more particularly made of metal.

The first insertion device present on the external side of the catheter shaft allows the simple insertion of a wire-like element into the former and hence into the lumen of the catheter from the outside. Here, the first insertion device is more particularly embodied such that the wire-like element is guided into the first lateral opening in the case of movement along the first insertion device on the external side of the catheter shaft. In the process, a transition between the first insertion device and the first lateral opening more particularly has a seamless and/or stepless design. If there are further lateral openings in addition to the first lateral opening, these advantageously also have a corresponding insertion device.

As a result of the insertion device, even very thin wire-like elements can be inserted first time into lateral openings with small diameters from the outside. Lateral openings in conventional catheters are usually designed to guide a guide wire, inserted from the distal end, out of the lumen to the outside. If there were the desire to insert a wire-like element into a lateral opening from the outside in the case of such a catheter, this could only be implemented in a protracted threading process and with the use of magnification lenses or the like.

The solution according to the invention allows the diameters of the lateral openings to be kept to a minimum, but wire-like elements can nevertheless still be easily inserted into the lateral openings. Lateral openings that are as small as possible contribute, inter alia, to the stability of the catheter shaft and the ability overall of the catheter to be inserted into the hollow organ.

The solution according to the invention provides an additional and practical option for introducing a wire-like element into the lumen of the catheter. Hence, wire-like elements can not only be inserted into the lumen from the proximal end of the catheter shaft as known, but can also just as feasibly be inserted through a lateral opening in the region of the distal end. This affords the possibility of implementing, in particular, novel and more efficient procedures when inserting wire-like elements into human and/or animal hollow organs for diagnostic, therapeutic, and/or surgical purposes. The catheters according to the invention can likewise overall be used in a more flexible fashion.

The catheter is advantageously designed as a single-lumen catheter. Such catheters can, in particular, be produced in a relatively straightforward fashion and can be manufactured with small dimensions. This allows a more flexible use of the catheter. However, in principle, the solution according to the invention can also be advantageous in the case of a multi-lumen catheter.

The first insertion device is advantageously situated in a region of the external side of the catheter shaft that faces the proximal end and adjoins the first lateral opening. As a result, the wire-like element can be inserted into the first lateral opening in the direction of the distal end from a proximal region. Since a wire-like element inserted into the lumen through a lateral opening usually also has to be pushed in the direction of the distal end, such an arrangement of the first insertion device makes the insertion overall of the wire-like element easier because the movement direction of the wire-like element in the first insertion device in the lumen is substantially directed in the same direction.

However, in principle it is also feasible to provide the first insertion device in, for example, a region of the external side of the catheter shaft that faces the distal end and adjoins the first lateral opening. The first insertion device can likewise in principle be present in a region lateral to the first lateral opening. However, in certain circumstances, the wire-like element must be pushed on in another direction after the insertion into the first lateral opening.

The first insertion device is preferably embodied as a guide trough that extends to the first lateral opening. In the process, the guide trough more particularly runs parallel to a longitudinal central axis of the lumen and, particularly preferably, a width of the guide trough substantially corresponds to a diameter of the first lateral opening. The guide trough is more particularly embodied as a concave indentation in the catheter shaft. A guide trough constitutes a relatively simple but nevertheless particularly expedient and compact guide device.

A guide trough is formed by e.g. two spaced-apart guide elements that, more particularly, are aligned parallel to one another. If the distal end of a wire-like element is pushed into the guide trough or space between the two guide elements and moved toward the lateral opening, the wire-like element is routed to the lateral opening, more particularly as a result of the two guide elements. If the width of the guide trough substantially corresponds to the diameter of the lateral opening, the wire-like element is automatically directed into the lateral opening.

Moreover, provision can also be made for a guide trough that protrudes over the first lateral opening in both proximal and distal direction. In this case, a wire-like element can be inserted into the lateral opening from optionally the proximal or the distal direction.

Moreover, the provision of a guide trough with two guide elements that are angled with respect to one another may also be advantageous, with a distance between the two guide elements continuously decreasing toward the lateral opening for example. This provides a conically tapered guide region between the two guide elements that may, in certain circumstances, simplify the insertion of the wire-like element into the guide trough. It is likewise feasible to form the guide trough in a direction that is oblique to the longitudinal central axis. However, this may make attaching and/or shaping the guide trough more difficult.

In principle, it is also feasible to provide as an insertion aid a funnel-shaped tube section that adjoins the lateral opening. However, in certain circumstances this can result in additional and projecting regions on the catheter shaft, which reduces the ability of the catheter to be inserted into a hollow organ.

The guide trough is particularly preferably embodied as a concavely arced region of the external side of the catheter shaft, wherein the concavely arced region preferably has a continuously increasing depth in the direction toward the distal end. The guide trough advantageously merges seamlessly and/or without steps or edges into the lateral opening.

It is relatively simple to introduce concavely arced regions into the external side of the catheter shaft. Thus, for example, the catheter shaft may be heated and reshaped with the aid of a wire piece pressed against the external side. If the guide trough is embodied as a concavely arced region of the external side, the projecting regions, e.g. projecting edges or steps, on the catheter shaft can moreover be reduced to a minimum, which is advantageous in respect of being able to insert it into hollow organs.

If the guide trough has a continuously increasing depth, it is possible, in particular, to implement a stepless transition from the external side to the guide trough. Moreover, in a region directly in front of the lateral opening, this results in a best-possible guide of the wire-like element to be inserted; this is advantageous in respect of being able to insert it into hollow organs.

However, in principle it is also feasible to attach e.g. two spaced-apart, rib-like projections to the external side of the catheter shaft as a guide trough or insertion device. However, this may in certain circumstances negate the aforementioned advantages of the concavely arced regions.

The first lateral opening is preferably aligned with the proximal end. In other words, a normal vector of an opening surface of the first lateral opening advantageously points away from the distal end and the normal vector is preferably at an angle to the longitudinal central axis of the lumen and/or catheter shaft.

Such an arrangement is particularly advantageous in conjunction with an insertion device that is present in a region of the external side of the catheter shaft that faces the proximal end and adjoins the first lateral opening. A wire-like element that is pushed through the insertion device in this case can thus be inserted into the lateral opening in an even simpler fashion because the lateral opening is tilted in the direction of the wire-like element moved through the insertion device.

Moreover, the bend of the wire-like element to be inserted is in the process reduced in the region of the lateral opening, which in turn lessens the frictional forces between the wire-like element and the lateral opening.

However, in principle the lateral opening can also be aligned perpendicularly to the longitudinal central axis. However, in certain circumstances the aforementioned advantages are negated in this case.

In a further preferred variant, a lateral first channel-like region, which opens into the first lateral opening, is formed in the lumen in a region of the first lateral opening such that a first passage region in the lumen remains free, more particularly next to the first channel-like region. In other words, there is, more particularly, a first so-called Y-switch or first branching in the lumen in the region of the first lateral opening. A section of the first channel-like region facing the distal end moreover advantageously runs substantially parallel to the longitudinal axis of the lumen.

A wire-like element, e.g. a guide wire, inserted into the lumen through the front opening can for example be directed into the channel-like region as a result of a bend in the catheter shaft, from which channel-like region it directly reaches the lateral opening. This can further increase the flexibility of the catheter according to the invention because a wire-like element can easily be guided both out of the lumen to the outside through the lateral opening and into the lumen from the outside through the lateral opening. The channel-like region advantageously has an internal diameter that is substantially matched to the external diameter of the wire-like element that should be passed through.

Alternatively, the wire-like element can be directed into the first passage region next to the first channel-like region, as a result of which the wire-like element can continue to be routed through the lumen in the direction of the proximal end. The first passage region advantageously has an internal diameter that is substantially matched to the external diameter of the wire-like element that should be passed through.

However, in principle a channel-like region can also be dispensed with or a differently designed device can be arranged for routing the wire-like element in the lumen. However, in certain circumstances this hinders the passage out of the lumen of the wire-like element to the outside through the lateral opening.

It is particularly preferred for an internal diameter of the lumen to be larger in a region between the distal end and the first lateral opening than in the remaining regions of the lumen. In the process, it is particularly preferable if the internal diameter of the lumen in the region between the distal end and the first lateral opening is embodied such that a wire-like element, e.g. a probe wire, that should be inserted using the catheter and a guide wire that should be used with the catheter have space next to one another in the lumen. As a result, the wire-like element and the guide wire can at the same time be present in the region between the distal end and the first lateral opening and/or be pushed past one another. This measure particularly increases the flexibility of the catheter according to the invention and reduces the dimensions of the catheter to a minimum in the other regions.

In a further advantageous variant, the internal diameter of the lumen in the region between the distal end and the first lateral opening is greater than the diameter of the first lateral opening by approximately a factor of 2-2.5 and/or greater than the minimum diameter of the first channel-like region by a factor of 2-2.5. Compared to the internal diameter of the first passage region, the internal diameter of the lumen in the region between the distal end and the first lateral opening is larger by approximately a factor of 1.75-2.25, preferably by a factor of 1.8-2.0.

However, in principle the lumen can also have a constant internal diameter. However, if it is selected to be so large that a wire-like element and the guide wire have space next to one another, this may in certain circumstances have a detrimental effect on the ability of the catheter to be inserted. If a diameter is too small, merely a single wire-like element has space in the lumen, which opposes the flexibility of the catheter during use.

There preferably is a tapered catheter tip at the distal end of the catheter. This can further improve the ability of the catheter to be inserted because constrictions in the hollow organs can be passed in an improved fashion. Here, a minimum internal diameter of the catheter tip is more particularly approximately equal to the internal diameter of the first passage region. Or rather, the internal diameter of the lumen in the region between the catheter tip and the first lateral opening is more particularly greater than the minimum internal diameter in the region of the catheter tip by approximately a factor of 1.75-2.25, preferably by a factor of 1.8-2.0. A catheter tip embodied thus can, in conjunction with correspondingly dimensioned wire-like elements, ensure that only a single wire-like element can be pushed through the catheter tip at any one time.

In a preferred embodiment, the catheter tip is more particularly formed by a preferably step-like, tapered end section of the catheter shaft and a hollow cylindrical tube piece, which is attached thereto in a coaxial fashion and on the end face. The hollow cylindrical tube piece more particularly has a constant internal diameter and is preferably made from a softer material than the catheter shaft. The hollow cylindrical tube piece particularly preferably comprises a proximal component that adjoins the catheter shaft and a distal component that adjoins the proximal component in the distal direction and forms the distal end of the catheter tip. In other words, the hollow cylindrical tube piece advantageously has a two-part design. Here, the distal component advantageously consists of a softer material than the proximal component. This further increases the ability of the catheter to be inserted because the catheter tip increases in hardness in the proximal direction. The distal component can be connected to the proximal component by e.g. a material connection technique, more particularly by welding.

In a particularly preferred embodiment, the proximal component has a bevel cut on its end facing the distal component, while the distal component likewise has a bevel cut on its end facing the proximal component. In the process, the bevel cuts are more particularly embodied such that the two components resting against one another with their end faces have a common longitudinal central axis, or form a straight hollow cylindrical body. With respect to a longitudinal central axis of the hollow cylindrical tube piece, the bevel cuts moreover are at an angle of, for example, 20-50°, preferably of approximately 25-35°. The bevel cuts soften the transition between a softer distal component and a harder proximal component, more particularly in the longitudinal direction, which is beneficial to the ability to be inserted.

However, it may also be advantageous to design the catheter tip to taper conically toward the distal end, at least in sections. In this case, for example, the distal and/or proximal component can be present in the form of a hollow cylindrical frustum.

However, in principle, use can also be made of an integral hollow cylindrical tube piece or such a tube piece can be dispensed with entirely such that the catheter tip is formed from e.g. merely a tapered distal end of the catheter shaft.

In principle, a catheter tip can also be dispensed with entirely, which reduces the ability to be inserted but simplifies the design of the catheter.

In a very particularly preferred variant, the catheter shaft has a second lateral opening that opens into the lumen, wherein the second lateral opening is spaced apart from the first lateral opening in a proximal direction. Here it is particularly preferred for the second lateral opening to be arranged diametrically opposite to the first lateral opening. Advantageously there additionally is, on the external side of the catheter shaft, a second insertion device for a second wire-like element that should be inserted into the second lateral opening from the outside. This can further economize the procedures when inserting wire-like elements into human and/or animal hollow organs for diagnostic, therapeutic, and/or surgical purposes and the catheters according to the invention can be used even more flexibly as a result.

Routing a plurality of wire-like elements is simplified if the two lateral openings are arranged diametrically opposite one another. This is because in this case the two wire-like elements can be routed through the lumen at opposing peripheries after passing through the respective lateral openings. This prevents the wire-like elements from crossing.

However, in principle it is also feasible for diametrically opposed lateral openings to be dispensed with and for the lateral openings to be arranged on a common side. However, this may, in certain circumstances, make it more difficult to route wire-like elements through the lumen. By way of example, if there are three or more lateral openings it may also be advantageous to distribute these evenly around the external side.

However, as illustrated above, it is also possible, in principle, to dispense with a second lateral opening. It is likewise feasible to provide more than two lateral openings. This affords the possibility of implementing even more complex procedures with a plurality of wire-like elements situated in the catheter at the same time.

Advantageously, the second insertion device for the second lateral opening substantially has the same design as the above-described first insertion device for the first lateral opening. As a result, a wire-like element can also be inserted into the lumen from the outside through the second lateral opening. The specific embodiments of the first insertion device can also accordingly be implemented in the second insertion device.

However, it is also feasible for the second insertion device to have a different design to the first insertion device, or it is even feasible to dispense with the second insertion device entirely. The alternatives and/or specific embodiments mentioned with respect to the first insertion device can also be implemented in the second insertion device. Optionally, this may simplify the production of the catheter. However, if the second insertion device is dispensed with entirely, the ability to insert a wire-like element into the second lateral opening from the outside may be severely hindered.

Moreover, a lateral second channel-like region, which opens into the second lateral opening, is preferably formed in the lumen in a region of the second lateral opening such that there is a second passage region of the lumen, more particularly next to the second channel-shaped region. In other words, there is, more particularly, a second Y-switch or second branching in the lumen in the region of the second lateral opening. A section of the second channel-like region facing the distal end likewise advantageously runs substantially parallel to the longitudinal axis of the lumen.

Like in the case of the first channel-like region, a wire-like element inserted into the lumen through the front opening and routed past and the first channel-like region or through the first passage region can be inserted into the second channel-like region as a result of e.g. a bend in the catheter shaft, from which second channel-like region it is directly directed into the second lateral opening. This can further increase the flexibility of the catheter according to the invention because wire-like elements can easily be routed both out of the lumen to the outside through the second lateral opening and into the lumen from the outside through the second lateral opening.

Alternatively, the wire-like element can be directed into the second passage region next to the second channel-like region, as a result of which the wire-like element reaches further through the lumen in the direction of the proximal end. The second passage region advantageously has an internal diameter that is substantially matched to the external diameter of the wire-like element or guide wire that should be passed through.

However, it is also within the scope of the invention to dispense with a second channel-like region, wherein, however, in certain circumstances the passage from the lumen to the outside of a wire-like element through the second lateral opening is made more difficult.

More preferably, there is an auxiliary wire, which is routed through the second lateral opening into the lumen and which protrudes into a region between the first lateral opening and the distal end, and so, more particularly, the first passage region of the lumen, situated next to the first channel-like region, is substantially blocked or sealed. More particularly, the auxiliary wire affords the possibility of substantially sealing the first passage region. A wire-like element, e.g. a guide wire, inserted into the lumen through the front opening, which is more particularly pushed past the distal end of the auxiliary wire is thereby directed automatically into the first channel-like region and leaves the lumen through the first lateral opening. A special bend of the catheter is not required for this.

The auxiliary wire is sufficiently fixed as a result of the fact that it protrudes into the region between the first lateral opening and the distal end. Thus, there is no need to fear it slipping out. However, in principle, the auxiliary wire can e.g. also have a shorter design such that it merely protrudes into the first channel-like region. However, this is less advantageous because a wire-like element advancing from the front opening is thus more likely to be able to line up behind the relatively immobile auxiliary wire.

In principle, it is likewise possible to insert the auxiliary wire into the first lateral opening. This can close off the first lateral output and a wire-like element inserted into the lumen through the front opening is automatically directed into the first passage region. Accordingly, it is also possible to apply an auxiliary wire to a first lateral opening in the case of a catheter with merely one first lateral opening.

In principle, it is also feasible to provide an auxiliary wire in both the first and the second lateral opening. However, in this case the auxiliary wire arranged in the second lateral opening advantageously only at most protrudes into the region between the first lateral opening and the second lateral opening. A wire-like element inserted into the lumen through the front opening is thereby automatically routed to the proximal end through the passage regions.

Advantageously, the auxiliary wire has a thickening situated outside of the second lateral opening, which thickening serves as a stop and prevents the auxiliary wire from completely passing through the second lateral opening. It goes without saying that the same also holds true if there is an auxiliary wire present in the first lateral opening. This prevents the auxiliary wire from being able to slip into the lumen through the lateral opening. More particularly, a thickening can be applied in a relatively straightforward fashion, for example by welding on plastic. The auxiliary wire is more particularly mainly made of metal.

However, other securing means are feasible in addition to the thickening, or in place thereof; for example the auxiliary wire can also be bent at its end protruding from the lateral opening such that its passage through the second lateral opening is made impossible and/or the auxiliary wire is wound around the external side of the catheter shaft.

It is particularly preferred for there to be a marking on the catheter shaft in a region of the first lateral opening and/or in a region of the second lateral opening, wherein the marking is more particularly embodied as a colored marking. By way of example, the marking can be a colored plastic element that was welded into the external side of the catheter shaft.

If there are two or more lateral openings, the markings are more particularly formed in a distinguishable fashion. As a result, the individual and usually very small lateral openings can be identified at once.

Advantageously, a marking is likewise applied in the region of the distal end or at the catheter tip, wherein this marking substantially corresponds to the markings arranged on the first and/or the second lateral opening. This clarifies the possible paths of the wire-like elements in the catheter shaft. In the process, it is possible, for example, to make a distal end of the catheter shaft or the catheter tip from a material that has a color corresponding to the marking on the first and/or the second lateral opening.

If there is a multipart catheter tip, which, for example, comprises a proximal component and a distal component, the distal component in particular is made from a material that has a color that corresponds to the marking of the first lateral opening. In this case, the proximal component is preferably made of a material that has a color that corresponds to that of the second lateral opening.

However, should it be expedient, the markings can also have a different design or these can even be dispensed with entirely. This may at best simplify the production of the catheter.

In a further advantageous aspect, a proximal section of the catheter shaft has a lower elasticity than a distal section of the catheter shaft. In other words, the proximal section of the catheter shaft preferably has a larger Young's modulus than the distal section of the catheter shaft. This aspect can be advantageous in general in catheters with a catheter shaft, independently of the design according to the invention. This can further improve the ability of the catheter to be inserted. This is because the more rigid proximal section improves the advance of the catheter in the hollow organ, while the distal section can nevertheless follow the profile of the hollow organ well as a result of the greater flexibility. However, in principle the catheter shaft can also have a substantially constant elasticity over the entire length.

It is particularly preferable for the proximal section of the catheter shaft to comprise a metal tubule while a distal section contains a plastic tubule. Here, the plastic tubule more particularly directly adjoins the metal tubule. In particular, the plastic tubule has a greater elasticity than the metal tubule. As a result of the combination of metal tubule and plastic tubule, it is possible once again to improve the ability of the catheter to be inserted in the case of an even more compact design. In the process, the metal tubule ensures a particularly effective advance of the catheter in a hollow organ, while the distal section with the plastic tubule is flexible in comparison thereto, and so the catheter can follow the hollow organ particularly well. However, such an embodiment is not mandatory. Other material combinations or an integral catheter shaft may also be advantageous, depending on the intended use of the catheter.

A ratio of the length of the metal tubule to the length of the plastic tubule preferably is 1.7-4.0. More particularly, the metal tubule has a length of 1.1-1.2 m, while the plastic tubule has a length that measures 30-40 cm. The metal tubule is advantageously made of steel, more particularly stainless steel. Such combinations of metal tubules and plastic tubules have been found to be optimal in respect of its ability to be inserted and obtaining a design of the catheter that is as compact as possible. However, other combinations with tubules with other dimensions are also feasible.

It is preferable for a support element to be provided in a transition region between the proximal section and the distal section of the catheter shaft, which support element is embodied such that a jump in elasticity between the proximal section and the distal section of the catheter shaft is reduced and/or at least partly compensated for. In particular, this can reduce the danger of kinking at the transition between the proximal section and the distal section of the catheter shaft. The support element is preferably a support wire. The support wire more particularly runs in the longitudinal direction of the catheter shaft. The support wire more particularly has a diameter of 0.10-0.50 mm, more particularly 0.30-0.35 mm. The support wire advantageously consists of steel, more particularly stainless steel. Steel was found to be particularly suitable for transition wires as a result of its material properties, more particularly its strength and flexibility. Other dimensions can also be advantageous, depending on material of the support wire and desired flexibility of the catheter.

Provision can also be made for another type of support element in place of a support wire, e.g. a tubule or a sheet-like, flat element, which more particularly can also be bent. Thus, the cross section of the support element need not necessarily be round, but can by all means also contain corners.

The support element or the support wire is more particularly attached to the proximal section of the catheter shaft or to the metal tubule, for example by welding, and protrudes into the internal region of the distal section of the plastic tubule. More particularly, the section of the support wire projecting from the proximal section or the metal tubule and protruding into the distal section or the plastic tubule has a length of 0.2-0.5 times, preferably 0.2-0.35 times the overall length of the plastic tubule. In the case of a plastic tubule with an overall length of 30-40 cm, the section of the support wire protruding into the plastic tubule for example measures 5-15 cm, preferably 8-12 cm, more preferably 9-11 cm. This can achieve optimal compensation of the jump in elasticity between the metal tubule and the plastic tubule. However, in principle, the support wire can also have other dimensions, provided this appears expedient.

It is particularly advantageous for the support element or the support wire to be attached to the metal tubule such that an inner cavity of the metal tubule remains completely free. This allows the best possible use of the inner cavity of the metal tubule, e.g. for passing through wire-like elements. In principle, however, the support element or the support wire can also be attached in the interior of the metal tubule. However, this may in certain circumstances hinder the passage of wire-like elements.

In order to attach the support element or the support wire, the metal tubule advantageously comprises a slit introduced into the metal tubule, which slit extends from the distal end of the metal tubule in the longitudinal direction of the metal tubule. The slit is embodied for partly holding the support element or the support wire and preferably has a width that corresponds to a diameter and/or a maximal width of the support element or support wire. As a result, the support element or the support wire can be fixed more easily in the slit and is at the same time at least partly embedded in the wall of the metal tubule, which allows a more compact design. In the longitudinal direction, the slit advantageously has a length of 0.01-0.05 times the overall length of the support wire. In an advantageous variant, the length of the slit is 1-5 mm, preferably 2.5-3.5 mm. As a result, the support wire can be attached in the slit in an optimum fashion.

However, in principle provision may also merely be made for a groove, which is introduced into the metal tubule from the outside, instead of the slit. It is likewise possible for the support element or the support wire to be applied to the metal tubule from the outside without a slit or a groove.

The support wire more particularly has a circular cross section. In an advantageous variant, the diameter of the support wire decreases in the distal direction, at least in a distal section. More particularly, the support wire has a conically tapered design, at least in a distal section. As a result, the elasticity of the support wire can be matched to the specific requirements, which allows the best possible compensation of the jump in elasticity between metal tubule and plastic tubule. The conically tapered distal section preferably has a length 0.2-0.4 times the overall length of the support wire, more particularly 2-4 cm.

In the case of a catheter with at least one lateral opening, the support element or the support wire at most extends in the distal direction to the proximal region of the at least one lateral opening. In the case of a plurality of lateral openings, the support element or the support wire more particularly at most extends in the distal direction to the furthest back lateral opening, which has the greatest distance from the distal end of the catheter. More particularly, the support element or the support wire extends in the distal direction to the at least one lateral opening or to the furthest back lateral opening. This ensures that the support element does not protrude into the regions of the at least one lateral opening and in the process hinder the insertion of wire-like elements. However, at the same time, this ensures an optimal compensation of the jump in elasticity between metal tubule and plastic tubule. More particularly, wire-like elements can thus also be inserted through the proximal end of the metal tubule and routed through the catheter shaft or the lumen, which extends the usage options for the catheter according to the invention.

In the case of catheters that have a lateral channel-like region, which opens into the at least one lateral opening, in the region of the at least one lateral opening in the lumen, the support element or the support wire is advantageously embodied such that the passage region in the lumen situated next to the channel-like region remains completely free. Thus the support element advantageously at most extends to the proximal end of the channel-like passage region of the at least one lateral opening. Correspondingly, said support element in the case of lateral openings at most extends to the proximal end of the channel-like passage region of the furthest back lateral opening.

However, in principle it is also possible to let the support element protrude into the region of the catheter tip for example, provided that this is expedient for specific applications. However, at best this reduces the usage options for the catheter.

It is particularly advantageous for the proximal end of the plastic tubule to be pushed onto the distal end of the metal tubule and attached to the distal end of the metal tubule, e.g. by pressure welding. If a support element, e.g. a support wire, is arranged, the plastic tubule advantageously completely surrounds the support element. If the support element or support wire is attached with a slit, the plastic tubule is more particularly arranged such that the slit is completely surrounded by the plastic tubule. As a result, the hollow organs are protected from the support element to the best possible extent during insertion of the catheter; this further improves its ability to be inserted.

However, in principle other arrangements are also feasible. Thus, the plastic tubule could be attached to the end side of the metal tubule by impact e.g. with the aid of a sleeve.

The catheter according to the invention is advantageously used as a set of instruments together with a guide wire and a special wire for diagnostic, surgical, and/or therapeutic purposes. As a result, the catheter can be matched to the guide wire and the special wire in an optimum fashion.

An external diameter of the guide wire and an external diameter of the special wire together advantageously at most have approximately the same size as the internal diameter of the lumen in the region between the distal end or catheter tip and the first lateral opening. This ensures that the guide wire and the special wire can be pushed past one another in this region. In order to ensure good displaceability, a certain amount of allowance is recommended in the internal diameter of the lumen in the region between the distal end or catheter tip and the first lateral opening.

However, it is also feasible for the internal diameter of the lumen to have a significantly larger design in the region between the distal end or catheter tip and the first lateral opening than the combination of the two external diameters of the two wires. However, this is disadvantageous in view of the smallest possible dimensions of the catheter shaft.

More particularly, the first lateral opening has a diameter that corresponds to the external diameter of the guide wire, while the second lateral opening has a diameter that corresponds to the external diameter of the special wire. As a result, the diameters of the two lateral openings can be kept as small as possible, as a result of which the catheter overall becomes more compact. However, it may also be advantageous for the diameters of the first and the second lateral opening to be substantially identical and embodied in accordance with the thicker of the two wires. This achieves the greatest possible amount of flexibility when using the instrument set because both the guide wire and the special wire can be inserted into the first and the second lateral opening. A certain amount of allowance in the dimensions of the lateral openings is also recommended in this case.

The special wire is more particularly embodied as a probe wire for a tomographic method, wherein, more particularly, this is a probe wire for optical coherence tomography. It was found that the catheter according to the invention or the set of instruments according to the invention is particularly advantageous in conjunction with tomographic methods, more particularly in bloodstreams. Very viscous contrast agents often have to be introduced into hollow organs in these methods in particular. The option of implementing novel and more efficient procedures in this case harbors great advantages.

However, in principle, it is also possible to use other special wires for diagnostic, therapeutic, and/or surgical methods with the catheter according to the invention.

The catheter according to the invention, or an instrument set with such a catheter, is particularly suited to application in diagnostic, therapeutic, and/or surgical methods in bloodstreams, which can be e.g. coronary arteries, peripheral blood vessels (in arms and/or legs), and/or blood vessels in the head.

In the case of an advantageous method, which is carried out e.g. for diagnostic purposes in a human and/or animal bloodstream, a wire-like element in particular, for example a, is inserted into the first lateral opening of a catheter according to the invention in a first step.

Further advantageous embodiments and combinations of features of the invention emerge from the following detailed description and the entirety of the patent claims.

BRIEF DESCRIPTION OF THE DRAWINGS

In the drawings used to explain the exemplary embodiment.

In principle, the same parts have in the figures been provided with the same reference signs.

WAYS OF IMPLEMENTING THE INVENTION

Figure 1:
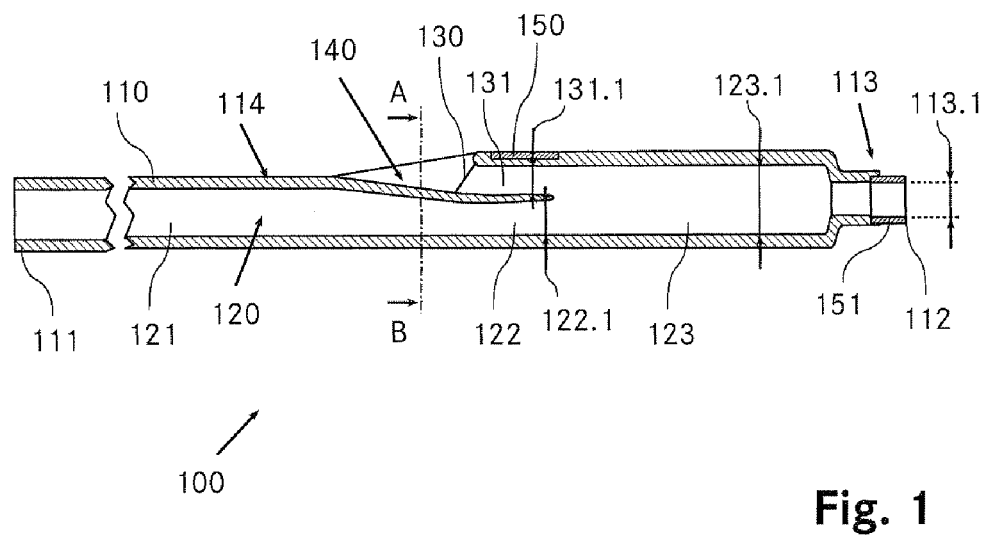
FIG. 1 shows a longitudinal section through a first catheter according to the invention with a single lateral opening.
Figure 2:
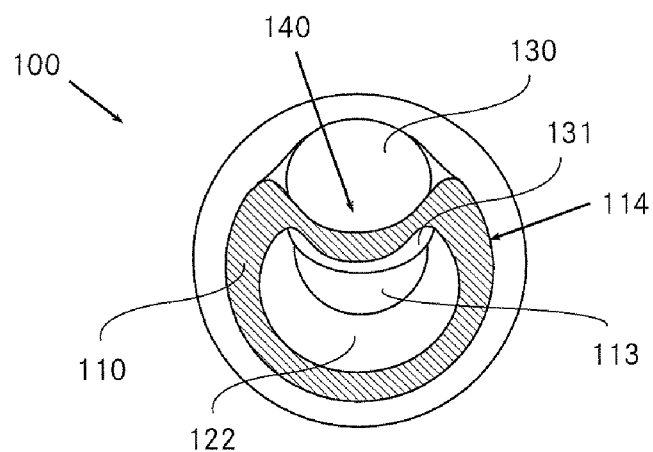
FIG. 2 shows a cross section through the catheter from FIG. 1 along the line A-B.

FIGS. 1 and 2 illustrate a first catheter 100 according to the invention in a longitudinal section and in a cross section. The first catheter 100 is a single-lumen catheter and comprises a catheter shaft 110 in the form of a substantially hollow-cylindrical tubule. The catheter shaft 110 consists of e.g. a plastic for catheters which is known per se. A lumen 120 or an internal and substantially cylindrical cavity in the catheter shaft 110 in this case extends from the proximal end 111 of the catheter shaft or the hollow cylindrical tubule to the distal end 112 thereof. In the region of the distal end 112, the catheter shaft 110 tapers in a step-like fashion to form a catheter tip 113. In this case, the catheter tip 113 has in the distal end thereof a hollow cylindrical tube piece 151 with a constant internal diameter, which is arranged coaxially and made from a softer material than the catheter shaft 110 and applied by pressure welding, for example. The hollow cylindrical tube piece 151 moreover has e.g. a red color and additionally serves as a marking.

In a region e.g. approximately 5-15 cm behind the distal end 112, an approximately circular lateral opening 130 is introduced laterally, on the external side 114, into the catheter shaft 110 or the hollow cylindrical tubule. Here the lateral opening 130 points toward the proximal end 111. A normal vector of the surface of the opening therefore is oblique with respect to the longitudinal axis of the catheter shaft 110. The lateral opening 130 opens into a distal region 123 of the lumen 120, situated behind the distal end 112, via a channel-like region 131 that runs in a direction toward the distal end 112 and approximately parallel to the longitudinal axis of the lumen 120. The channel-like region 131 is introduced into a lateral surface of the lumen 120 and has a cylindrical cavity with an internal diameter 131.1 that is substantially constant over its length. The internal diameter 131.1 of the channel-like region 131 in this case approximately corresponds to the diameter of the lateral opening 130. In addition to the channel-like region 131, the lumen 120 contains a passage region 122 with a minimum internal diameter 122.1 such that a proximal region 121 of the lumen 120, adjoining the lateral opening 130 in the proximal direction, communicates with the distal region 123 in front of the lateral opening 130 and in front of the channel-like region 131.

In a region of the external side 114, which adjoins the lateral opening 130 in the longitudinal direction and faces the proximal end 111, there moreover is a guide trough 140 formed into said external side 114 of the catheter shaft 110 as an insertion device for a wire-like element. The guide trough 140 is embodied as a concavely arced or tub-shaped indentation in the catheter shaft 110 and has an increasing depth in the direction toward the lateral opening 130. Here the transition between the guide trough 140 and the lateral opening 130 and the transition between the guide trough 140 and the region of the external side 114 adjoining the guide trough 140 is embodied seamlessly and without steps.

A marking 150 in the form of an e.g. red color segment made of plastic has been introduced into the catheter shaft 110 in a region facing the distal end 112 and adjoining the lateral opening 130. The marking 150 or the red color segment is attached by e.g. pressure welding, and so there are no edges, projections or seams. The color of the marking 150 and the color of the hollow cylindrical tube piece 151, which likewise serves as a marking, are substantially identical.

The catheter tip 113 has a minimum internal diameter 113.1 that for example measures approximately 0.51 mm while the distal region 123 of the lumen 120, or the region between the lateral opening 130 and the catheter tip 113, has an internal diameter 123.1 of e.g. approximately 0.92 mm. The internal diameter 131.1 of the channel-like region 131 measures e.g. approximately 0.41 mm while the minimum internal diameter 122.1 of the passage region 122 e.g. is approximately 0.51 mm. In the proximal region 121 of the lumen 120, the internal diameter for example is at least approximately 0.52 mm. By way of example, the wall of the catheter shaft 110 has a strength that measures approximately 0.08-0.12 mm. The internal diameter 131.1 of the channel-like region 130 and the minimal internal diameter 122.1 of the passage region 122 together have approximately the same size as the internal diameter 123.1 of the distal region 123.

Figure 3:
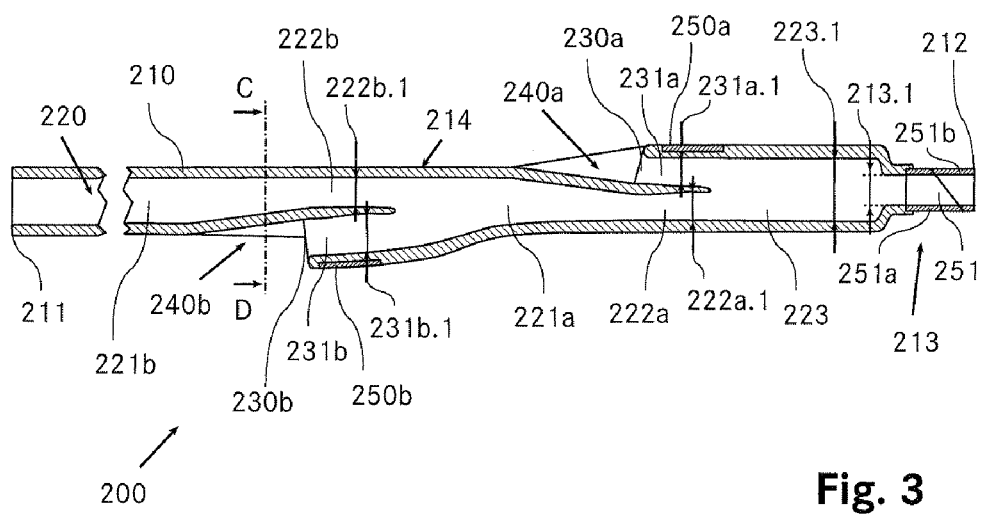
FIG. 3 shows a longitudinal section through a second catheter according to the invention with two spaced-apart and diametrically opposed lateral openings.
Figure 4:
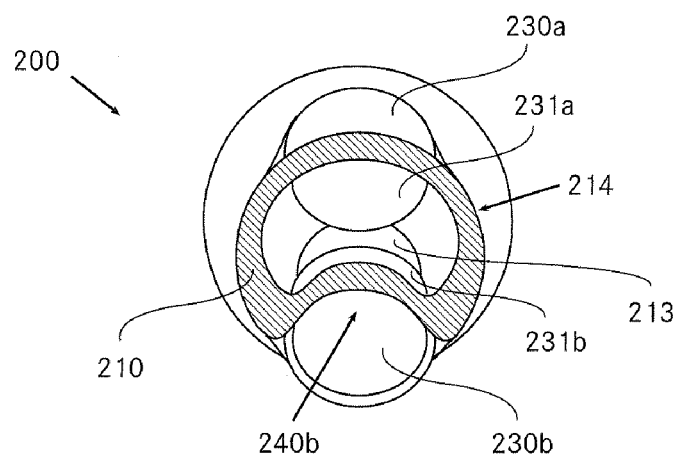
FIG. 4 shows a cross section through the catheter from FIG. 3 along the line C-D.

FIGS. 3 and 4 show a second catheter 200 according to the invention in a longitudinal section and in a cross section. Like the first catheter 100, the second catheter 200 is also a single-lumen catheter and comprises a catheter shaft 210 in the form of a substantially hollow-cylindrical tubule. The catheter shaft 210 consists of e.g. a plastic for catheters which is known per se. A lumen 220 or an internal and substantially cylindrical cavity in the catheter shaft 210 in this case extends from the proximal end 211 of the catheter shaft or the hollow cylindrical tubule to the distal end 212 thereof. In the region of the distal end 212, the catheter shaft 210 tapers in a step-like fashion to form a catheter tip 213. In this case, the catheter tip 213 has in the distal end thereof a hollow cylindrical tube piece 251 with a constant internal diameter, which is arranged coaxially. The hollow cylindrical tube piece 251 in this case has a proximal component 251a, which on its end face is welded onto the tapered end of the catheter shaft 210. A distal end of the proximal component 251a is formed obliquely, for example at an angle of approximately 30°, with respect to the longitudinal axis of the catheter. In other words, the proximal component 251a has a bevel cut at its distal end. Coaxially, there is a distal component 251b of the hollow cylindrical tube piece 251 at the distal end of the proximal component 251a. In this case, the proximal end of the distal component 251b is likewise oblique, or formed at an angle of approximately 30°. The two components are welded together by a material connection.

The distal component 251b is made from a softer material than the proximal component 251b, which in turn is made from a softer material than the catheter shaft 210. By way of example, the distal component 251b material moreover has a red color, which serves as a marking. The material of the proximal component 251a has e.g. a black color, which likewise serves as a marking.

In a region e.g. approximately 5-15 cm behind the distal end 212, an approximately circular first lateral opening 230a is introduced laterally, on the external side 214, into the catheter shaft 210 or the hollow cylindrical tubule. Here the first lateral opening 230a points toward the proximal end 211. A normal vector of the surface of the opening therefore is oblique with respect to the longitudinal axis of the catheter shaft 210. The first lateral opening 230a opens into a distal region 223 of the lumen 220, situated behind the distal end 212, via a first channel-like region 231a that runs in a direction toward the distal end 212 and approximately parallel to the longitudinal axis of the lumen 220. The first channel-like region 231a is introduced into a lateral surface of the lumen 220 and has a cylindrical cavity with an internal diameter 231a.1 that is substantially constant over the length of said cavity. The internal diameter 231a.1 of the first channel-like region 231a in this case approximately corresponds to the diameter of the first lateral opening 230a. In addition to the first channel-like region 231a, the lumen 220 contains a first passage region 222a with a minimum internal diameter 222a.1.

In a region of the external side 214, which adjoins the first lateral opening 230a in the longitudinal direction and faces the proximal end 211, there moreover is a first guide trough 240a formed into said external side 214 of the catheter shaft 210 as an insertion device for a wire-like element. The first guide trough 240a is embodied as a concavely arced or tub-shaped indentation in the catheter shaft 210 and has an increasing depth in the direction toward the first lateral opening 230a. Here the transition between the first guide trough 240a and the first lateral opening 230a and the transition between the first guide trough 240a and the region of the external side 214 adjoining the first guide trough 240a is embodied seamlessly and without steps.

In a region e.g. approximately 2-5 cm away from the first lateral opening 240a in the proximal direction, an approximately circular second lateral opening 230b is introduced laterally, on the external side 214, into the catheter shaft 210 or the hollow cylindrical tubule, diametrically opposite to the first lateral opening 240a. Here the second lateral opening 230b likewise points toward the proximal end 211. A normal vector of the surface of the opening therefore is oblique with respect to the longitudinal axis of the catheter shaft 210. The second lateral opening 230b opens into a region 221a between the first lateral opening 240a and the second lateral opening 240b of the lumen 220 via a second channel-like region 231b that runs in a direction toward the distal end 212 and approximately parallel to the longitudinal axis of the lumen 220. The second channel-like region 231b is introduced into a lateral surface of the lumen 220 opposite to the first channel-like region 231a and has a cylindrical cavity with an internal diameter 231b.1 that is substantially constant over the length of said cavity. The internal diameter 231b.1 of the second channel-like region 231b in this case approximately corresponds to the diameter of the second lateral opening 230b. In addition to the second channel-like region 231b, the lumen 220 contains a second passage region 222b with a minimum internal diameter 222b.1 such that a proximal region 221b of the lumen 220, adjoining the second lateral opening 230b in the proximal direction, communicates with the region 221a between the first lateral opening 240a and the second lateral opening 240b. Therefore the first passage region 222a results in a continuous connection between the proximal region 221b and the distal region 223, which is in front of the first lateral opening 240a or in front of the first channel-like region 230a.

In a region of the external side 214, which adjoins the second lateral opening 230b in the longitudinal direction and faces the proximal end 211, there moreover is a second guide trough 240b formed into said external side 214 of the catheter shaft 210 as an insertion device for a wire-like element. The second guide trough 240b is embodied as a concavely arced or tub-shaped indentation in the catheter shaft 210 and has an increasing depth in the direction toward the second lateral opening 230b. Here the transition between the second guide trough 240b and the second lateral opening 230b and the transition between the second guide trough 240b and the region of the external side 214 adjoining the second guide trough 240b is embodied seamlessly and without steps.

A first marking 250a in the form of an e.g. red color segment made of plastic has been introduced into the catheter shaft 210 in a region facing the distal end 112 and adjoining the first lateral opening 230a. Likewise, a second marking 250b in the form of an e.g. black color segment made of plastic has been introduced into the catheter shaft 210 in a region facing the distal end 112 and adjoining the second lateral opening 230*b*.

The color of the first marking 250*a* and the color of the distal component 251*a* are substantially identical in this case, i.e. they have e.g. the same red color, in order to highlight the passage from the first lateral opening 230*a* to the catheter tip 213. The color of the second marking 250*b* and the color of the proximal component 251*b* are likewise substantially identical in this case, i.e. they have e.g. the same black color, in order to highlight the passage from the second lateral opening 230*b* to the catheter tip 213. The two markings 250*a*, 250*b*, or the colored segments, are applied by e.g. pressure welding, and so there are no edges, projections or seams.

The catheter tip 213 has a minimum diameter 213.1 that for example measures approximately 0.51 mm while the distal region 223 of the lumen 220, or the region between the first lateral opening 230*a* and the catheter tip 213, has an internal diameter 223.1 of e.g. approximately 0.92 mm. The internal diameter 231*a*.1 of the first channel-like region 231*a* measures e.g. approximately 0.41 mm while the minimum internal diameter 222*a*.1 of the first passage region 222*a* e.g. is approximately 0.51 mm. In the region 221*a* between the first lateral opening 230*a* and the second lateral opening 230*b*, the internal diameter of the lumen 220 for example is at least approximately 0.52 mm.

The internal diameter 231*b*.1 of the second channel-like region 231*b* measures e.g. approximately 0.41 mm while the minimum internal diameter 222*a*.1 of the second passage region 222*a* e.g. is approximately 0.51 mm. The proximal region 221*b* of the lumen 220 adjoining the second lateral opening 230*b* for example has an internal diameter of e.g. at least approximately 0.52 mm.

The internal diameter 231*b*.1 of the second channel-like region 231*b* and the minimum internal diameter 222*b*.1 of the second passage region 222*b* together likewise have approximately the same size as the internal diameter 223.1 of the distal region 223. By way of example, the wall of the catheter shaft 210 has a strength that measures approximately 0.08-0.12 mm.

Figure 5:
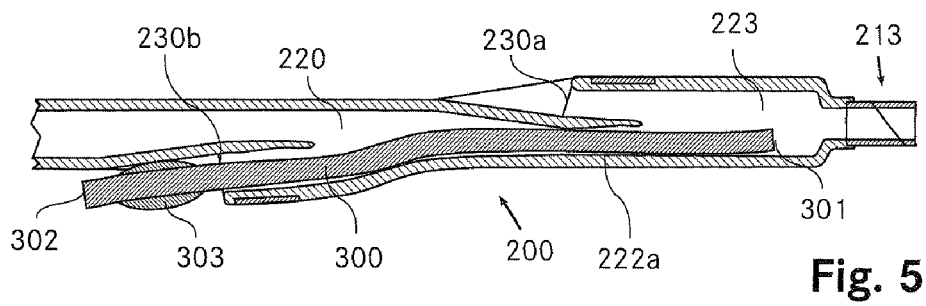
FIG. 5 shows the catheter from FIGS. 3 and 4 with an auxiliary wire introduced into the back lateral opening.

FIG. 5 shows the second catheter 200 from FIGS. 3 and 4 with an auxiliary wire 300 inserted into the second lateral opening 230*b* from the outside. Here, the auxiliary wire has been passed through the first passage region 222*a* and a front end 301 of the auxiliary wire 300 is in the distal region 223 of the lumen behind the catheter tip 213. A thickening 303 is arranged at the back end 302, which lies outside of the catheter shaft, of the auxiliary wire 300. Here, the thickening has a minimum diameter that is greater than a diameter of the second lateral opening 230*b*, and so the auxiliary wire 300 is prevented from slipping into the lumen 220 in its entirety. Ideally, the auxiliary wire has a diameter that approximately corresponds to the minimum internal diameter 222*a*.1 of the first passage region 222*a*, and so the latter is substantially sealed or blocked in respect of passing through further wire-like elements.

Figure 6:
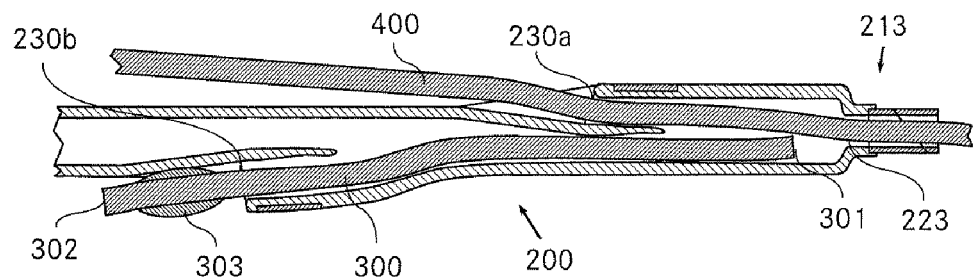
FIG. 6 shows the catheter from FIG. 5 on a guide wire running through the front lateral opening.
Figure 7:
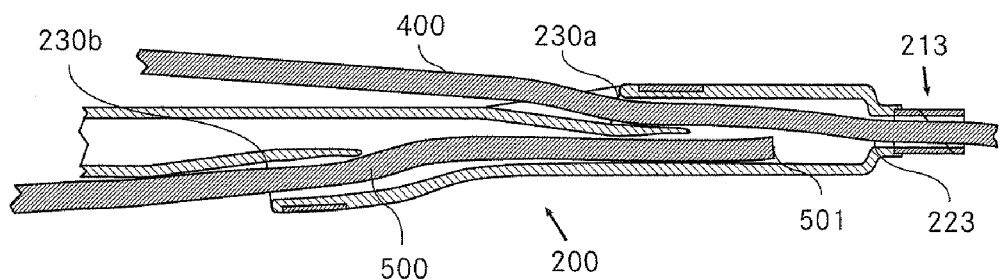
FIG. 7 shows the catheter from FIG. 6 with a probe wire inserted through the back lateral opening.
Figure 8:
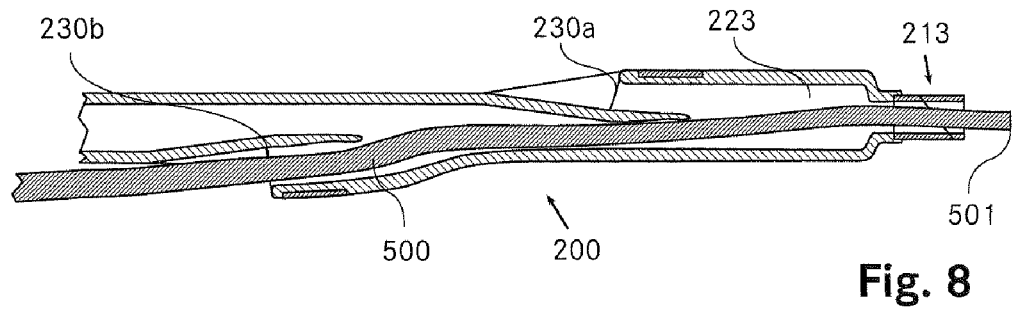
FIG. 8 shows the catheter from FIG. 7, wherein the guide wire was advanced into the lumen of the catheter and the probe wire was advanced forward through the catheter tip.

FIGS. 6-8 illustrate an advantageous use of the catheter 200, shown in FIG. 5, with an inserted auxiliary wire 500. In the process, the following method steps are undertaken:

In a first method step, the catheter 200 shown in FIG. 5 is provided with an auxiliary wire 500 inserted into the second lateral opening 230*b*. Here, the second catheter 200 is advantageously a component of an instrument set, which also comprises a guide wire 400 and a probe wire 500 in addition to the second catheter 200.

In a second method step, the back end of a guide wire 400, the front end of which has already been positioned in e.g. a bloodstream, is threaded through the front opening or the catheter tip 213 and pushed into the distal region 223. The guide wire has a diameter of e.g. 0.36 mm. The front end is now pushed past the auxiliary wire 300 and thereby automatically directed into the first channel-like region 231*a*, and from there it is routed out of the lumen 220 through the first lateral opening 230*a*. The situation present now is illustrated in FIG. 6.

Subsequently, the auxiliary wire 300 is pulled out of the second lateral opening 230*b* in a third method step and removed.

In a subsequent fourth method step, a wire-like element in the form of a probe wire 500 for optical coherence tomography is now pushed into the second lateral opening 230*b* with the aid of the second guide trough 240*b* until the front end 501 of the probe wire comes to rest next to the guide wire 400 in the distal region 223 of the lumen 220. This situation is illustrated in FIG. 7. The probe wire has a diameter of e.g. approximately 0.49 mm.

The second catheter 200 is subsequently in the fifth method step pushed along the guide wire 400, through a possibly present coronary catheter, and into the desired position in the bloodstream. In the process, the probe wire maintains its relative position in the lumen 220 of the second catheter 200.

The guide wire 400 is retracted in a sixth method step such that the front end 401 of the guide wire comes to rest in the distal region 223 behind the catheter tip 213 or between the first lateral opening 230*b* and catheter tip 213. Alternatively, the guide wire 400 can also be entirely removed from the catheter 200 and/or the bloodstream.

The probe wire 500 is subsequently pushed out of the catheter tip 213 toward the front in the seventh method step. This situation corresponds to FIG. 8.

The second catheter 200 can now, along the probe wire 500, be entirely pulled out of the bloodstream and a possible coronary catheter in the eighth method step. Thus it is only the probe wire 500 that remains in the bloodstream. This also allows the problem-free introduction of e.g. highly viscous contrast agents into the bloodstream. The access through a possibly present coronary catheter is hardly adversely affected by the probe wire 500 situated therein.

In a ninth method step, the probe wire 500 can be entirely withdrawn after the treatment has been completed. However, alternatively, the second catheter 200 can also again be advanced into the bloodstream after the treatment along the probe wire 500, which now acts as a guide wire for the catheter, has ended. It is subsequently possible for e.g. the probe wire 500 to be retracted into the distal region 223 and the guide wire 400 to be once again pushed out of the catheter tip 213 such that it for example again comes to rest in its original position. This once again substantially results in the situation shown in FIG. 8.

Then the second catheter 200 with the probe wire 500 can be retracted along the guide wire 400 in a possible further method step.

If desired, the second catheter 200 can now be equipped with, for example, a further wire-like element and it is once again correspondingly possible to start at the second method step.

Figure 9:
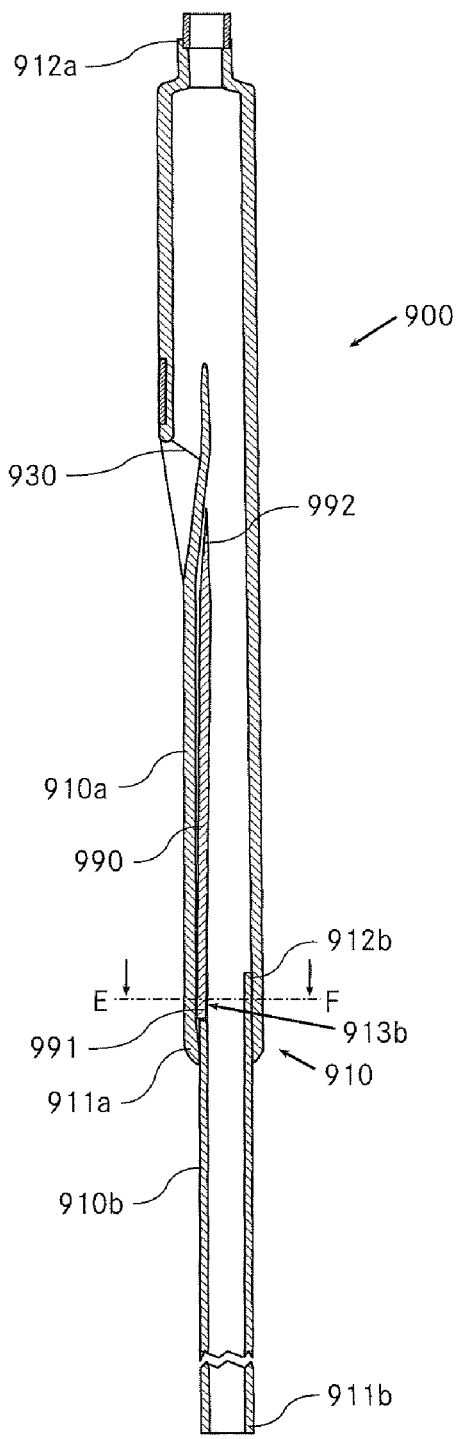
FIG. 9 shows a longitudinal section through a third catheter according to the invention with a two-part catheter shaft comprising a metal tubule and a plastic tubule, wherein a support element for compensating for the jump in elasticity is arranged in the transition region between the two tubules.
Figure 10:
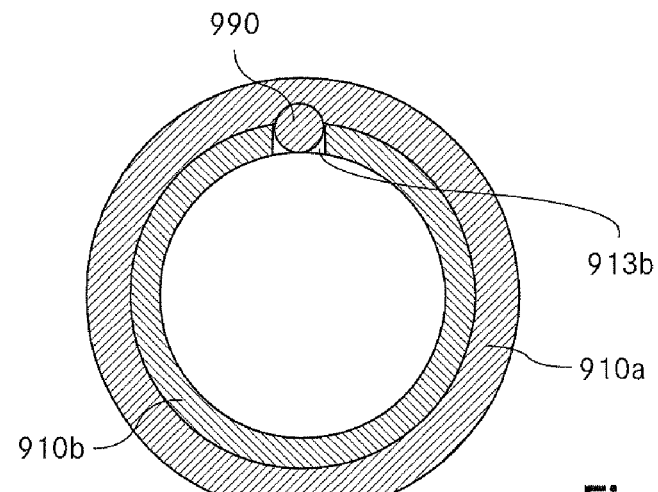
FIG. 10 shows a cross section through the catheter from FIG. 9 along the line E-F.

If there merely is one lateral opening, as is the case in the first catheter 100, it is possible, for example, to carry out the following method:

FIG. 9 comprises a third catheter 900 according to the invention in a longitudinal section along the longitudinal axis. FIG. 10 represents a cross section through the third catheter 900 along the line E-F in FIG. 9. Apart from the catheter shaft 910, the third catheter 900 substantially has the same design as the first catheter 100 from FIGS. 1 and 2.

The catheter shaft 910 in the third catheter 900 consists of a distal section made of a hollow cylindrical plastic tubule 910*a* and, adjoining it, a proximal section made of a hollow cylindrical metal tubule 910*b* made of stainless steel.

A slit 913*b* has been introduced into the metal tubule 910*b* at the distal end 912*b* of the metal tubule 910*b*. In this case, the slit 913*b* extends in the longitudinal direction of the metal tubule 910*b* from the end face at the distal end 912*b*. Arranged in the slit 913*b* there is the proximal end 991 of a support wire 990, which end has a material connection with the metal tubule as a result of laser welding. Here, the support wire 990 acts as support element. The support wire 990 protrudes into the plastic tubule 910*a* in the distal direction and reduces the jump in elasticity between metal tubule 910*b* and plastic tubule 910*a* such that the catheter 900 is more readily able to be inserted into a hollow organ. In the distal direction, the distal end 992 of the support wire 990 is directly in front of the lateral opening 130. In other words, the support wire 990 protrudes up to the proximal region of the at least one lateral opening 130.

The section of the support wire 990 protruding into the plastic tubule corresponds to approximately 0.2-0.3 times the overall length of the plastic tubule 910*a*, wherein the plastic tubule 910*a* has an overall length of 30-40 cm. Here, the overall length of the plastic tubule 910*a* is measured from the proximal end 911*a* to the distal end 912*a*. By way of example, an overall length of the metal tubule 910*b* measures 1.1-1.2 m.

The proximal end 911*a* of the plastic tubule 910*a* is pushed over the distal end 912*b* of the metal tubule 910*b* and connected to the latter by pressure welding. In the process, the distal proximal end 911*a* is in the proximal direction also pushed over the slit 913*b* and the support wire 990, which is held and attached therein, and so there is a fluid-tight connection between the plastic tubules 910*a* and the metal tubule 910*b*.

Figure 11:
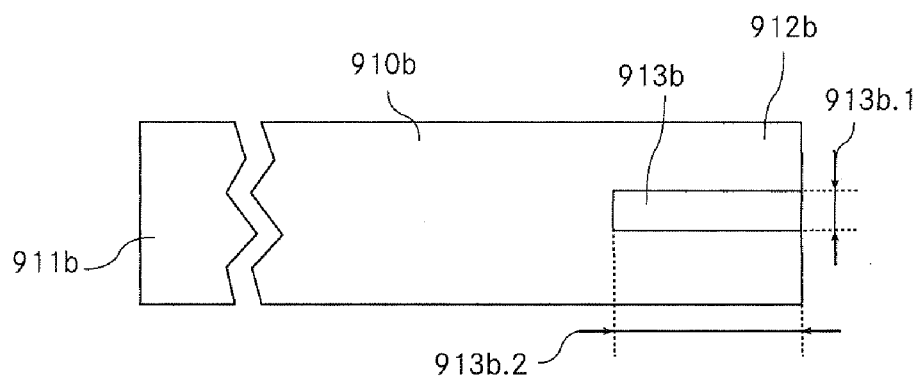
FIG. 11 shows a plan view of the metal tubule of the catheter from FIG. 9 with a slit, applied to the end side, for holding the support element.

In order to clarify the design, FIG. 11 shows a plan view of the metal tubule 910*b* before the assembly of the third catheter 900. The slit 913*b* for holding the support wire 990 has a length 913*b*.2 of approximately 3 mm measured in the longitudinal direction. The slit has a width (measured perpendicularly to the longitudinal direction) of approximately 0.33 mm.

Figure 12:
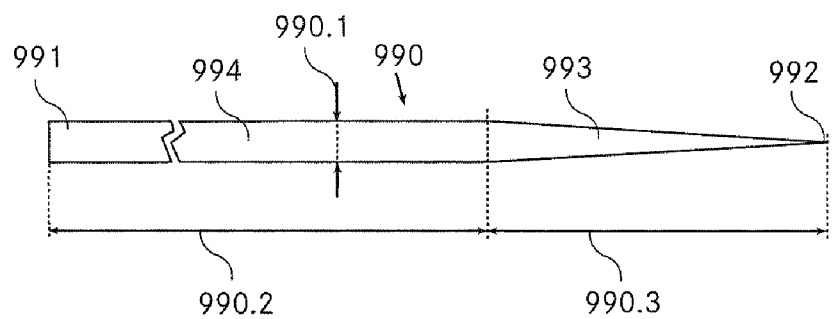
FIG. 12 shows a plan view of the support element of the catheter from FIG. 9.

FIG. 12 correspondingly shows the support wire 990 before the assembly of the catheter 900. The support wire 990 has a section 993 that tapers in a conical shape toward the distal end 992. The conically shaped tapering section 993 has a length of approximately 3 cm. In the proximal direction, the conically shaped tapering section 993 is adjoined by a cylindrical section 994 with a circular cross section and a constant diameter 990.1 of approximately 0.33 mm and which extends to the proximal end 991 of the support wire 990. The cylindrical section 994 has a length 990.2 of approximately 7 cm. Hence, the support wire 990 has an overall length, i.e. the length 990.2 of the cylindrical section 994 plus the length 990.3 of the conically shaped tapering section 993, that measures approximately 10 cm. Accordingly, the length 990.3 of the conically shaped tapering distal section 993 corresponds to approximately 0.3 times the overall length of the support wire 990.

The length 913*b*.2 of the slit 913 in the longitudinal direction corresponds to approximately 0.03 times the overall length of the support wire 990 while the width 913*b*.1 of the slit 913 corresponds approximately to the diameter 990.1 of the support wire 990 in the cylindrical section 994.

The first catheter 100 from FIGS. 1 and 2 can for example be used as follows:

A wire-like element, e.g. a probe wire for optical coherence tomography, is, whilst outside the human and/or animal body, inserted into the lumen 220 from the outside through the lateral opening 130 of the first catheter 100 and pushed into the region 123 between lateral opening 130 and distal end 112.

At the front opening at the distal end 112 or the catheter tip 113, the first catheter 100 is pushed onto the proximal end of a guide wire already positioned in the hollow organ.

The first catheter 100 is now pushed into the hollow organ along the guide wire and positioned, wherein the guide wire in the lumen 220 is pushed through the passage region 122 in the direction of the proximal end 111 of the catheter shaft, past the wire-like element and the lateral opening 130. Here, the distal region 123 is more particularly dimensioned such that the guide wire and the wire-like element have space next to one another and can be displaced with respect to one other. During the movement along the guide wire, the wire-like element maintains its position relative to the lateral opening 130 or the distal end 112 of the catheter shaft 110. The guide wire moreover advantageously has a sufficient length such that the first catheter 100 can already be pushed on the guide wire in its entirety outside of the human or animal body. As a result, the guide wire can be held when the first catheter 100 is moved.

Once the first catheter has been positioned in the hollow organ, the guide wire is completely withdrawn and removed if necessary.

Now the wire-like element, or the probe wire, is advanced to the extent that it emerges from the front opening or from the catheter tip 113.

It is thereupon possible to retract the first catheter along the wire-like element. Since it is only the relatively short section between the lateral opening 130 and the distal end 112 that is threaded onto the wire-like element or the probe wire, the catheter 100 can be withdrawn from the hollow organ in its entirety without problems. It is merely the wire-like element or probe wire that remains in the hollow organ, e.g. in a bloodstream.

The aforementioned exemplary embodiments and uses should merely serve as illustrative examples, which may be modified as desired within the scope of the invention.

Thus, for example, it is possible to provide additional lateral openings in both catheters 100, 200, which additional lateral openings serve for e.g. introducing fluids and/or suctioning these away. It is likewise possible to provide additional elements on the catheters. Possible elements include, for example, special catheter tips, balloons that can be actuated, radiopaque markings and/or additional lumens in the catheter shaft. Radiopaque markings can be introduced into the catheter shaft 110, 210 at the catheter tip, for example in a region behind the hollow cylindrical tube pieces 151, 251.

Moreover, if desired, the catheter tips 113, 213 can be dispensed with, and so there are openings at the distal ends 112, 212 of the two catheters 100, 200 that correspond to the internal diameter of the distal regions 113, 223. It is also possible to provide a catheter tip that tapers conically to the distal end in place of a step-like tapering catheter tip.

It is also possible to dispense with the hollow cylindrical tube pieces 151, 251.

In addition to the colored materials of the hollow cylindrical tube pieces 151, 251, or in place thereof, it is also possible to apply other markings, e.g. directly on the catheter shaft 110, 210, in the region of the distal end.

In the case of the second catheter 200, the two lateral openings 230a, 230b can also be present e.g. on the same side of the catheter shaft rather than lying diametrically opposite one another. Furthermore, the distances between the two lateral openings can also vary over broader ranges. It is likewise possible to provide at least one additional lateral opening for introducing wire-like elements, which likewise has an insertion device or insertion trough.

It also lies within the scope of the invention to adjust the two insertion devices 240a, 240b differently and e.g. to a particular type of wire-like elements.

The lateral openings 230a, 230b of the second catheter 200 may also be available with different dimensions such that, for example, a specific wire-like element can only be passed through at one of the two lateral openings 230a, 230b.

In principle, the support wire 990 of the third catheter 900 can also have an oval or elliptic cross section, or a cross section that is not round. The conically shaped tapered section 993 may also be longer or shorter. It is likewise possible to provide on the support wire 990 a section that tapers in a step-like fashion in addition to the conically shaped tapered section 993, or in place thereof.

Moreover, the second catheter 200 from FIG. 3 can also be equipped with a two-part shaft as in the third catheter 90. Accordingly, a support wire can also be arranged in the second catheter 200 in this case. Said support wire advantageously at most protrudes up to the proximal section of the second lateral opening 230b.

The described methods can moreover be fitted to specific conditions without restrictions. Thus, individual method steps may be omitted or replaced by other method steps, and/or the sequences of the individual method steps may be modified if this is expedient.

In conclusion, it should be noted that a novel catheter is provided, which can be used in a more flexible fashion and allows more efficient and simpler method steps to be carried out when introducing wire-like elements into human and/or animal hollow organs.

The invention claimed is:

1. A single-lumen catheter for insertion into a human or animal hollow organ, comprising
   a) a catheter shaft with a lumen, which opens into a front opening at a distal end of the catheter shaft,
   b) wherein the catheter shaft has at least a first lateral opening that is at a distance from the distal end and opens into the lumen,
   c) at least a first insertion device, arranged on an external side of the catheter shaft in a region of the first lateral opening, for a wire-like element that should be inserted into the first lateral opening from the outside
   d) a second lateral opening that opens into the lumen such that during an exchange of a first wire-like element for a second wire-like element the both wire-like elements can be simultaneously in the catheter,
   e) wherein the second lateral opening is spaced apart from the first lateral opening in a proximal direction, and
   f) the second lateral opening is arranged diametrically opposed to the first lateral opening.

2. The catheter as claimed in claim 1, characterized in that the first insertion device is in a region of the external side of the catheter shaft that faces the proximal end and adjoins the first lateral opening.

3. The catheter as claimed in claim 1, characterized in that the first lateral opening and the second lateral opening are aligned with the proximal end, respectively.

4. The catheter as claimed in claim 1, characterized in that a lateral first channel-like region, which opens into the first lateral opening, is formed in the lumen in a region of the first lateral opening such that a first passage region in the lumen remains free, wherein a section of the first channel-like region facing the distal end runs substantially parallel to the longitudinal axis of the lumen.

5. The catheter as claimed in claim 1, characterized in that an internal diameter of the lumen is larger in a region between the distal end and the first lateral opening than in the remaining regions of the lumen.

6. The catheter as claimed in claim 1, characterized in that there is a tapered catheter tip at the distal end, wherein the catheter tip is formed by a step-like tapered end section of the catheter shaft and a hollow cylindrical tube piece, which is attached thereto in a coaxial fashion and on the end face, and wherein the hollow cylindrical tube piece has a two-part design.

7. The catheter as claimed in claim 1, characterized in that there is a second insertion device for a second wire-like element on the external side of the catheter shaft, that should be inserted into the second lateral opening from the outside.

8. The catheter as claimed in claim 7, characterized in that the second insertion device for the second lateral opening substantially has the same design as the first insertion device for the first lateral opening.

9. The catheter as claimed in claim 7, characterized in that the first insertion device and the second insertion device are embodied as guides trough that extend to the first lateral opening and the second lateral opening, respectively, and wherein the guides trough run parallel to a longitudinal central axis of the lumen and a width of the guides trough substantially corresponds to a diameter of the first lateral opening and the second lateral opening, respectively.

10. The catheter as claimed in claim 9, characterized in that the guide trough is embodied as a concavely arced region of the external side of the catheter shaft, wherein the concavely arced region has a continuously increasing depth in the direction toward the distal end.

11. The catheter as claimed in claim 1, characterized in that there is an auxiliary wire, which is routed through the second lateral opening into the lumen and which projects into the region between the first lateral opening and distal end, and so the first passage region of the lumen, situated next to the first channel-like region, is blocked, and that the auxiliary wire has a thickening situated outside of the second lateral opening, which thickening serves as a stop and prevents the auxiliary wire from completely passing through the second lateral opening.

12. The catheter as claimed in claim 1, characterized in that there is a marking on the catheter shaft in a region of the first lateral opening and in a region of the second lateral opening, respectively, wherein the marking is embodied as a colored marking.

13. The catheter as claimed in claim 1, characterized in that a proximal section of the catheter shaft has a lower elasticity than a distal section of the catheter shaft, wherein the proximal section of the catheter shaft comprises a metal tubule and the distal section of the catheter shaft contains a plastic tubule.

14. The catheter as claimed in claim 13, characterized in that a support element like a support wire running in the longitudinal direction, is arranged in a transition region between the proximal section and the distal section of the catheter shaft, wherein the support element is embodied such that a jump in elasticity between the proximal section and the distal section of the catheter shaft is reduced or at least partly compensated for.

15. The catheter as claimed in claim 14, characterized in that the support element is a support wire, which is attached to the metal tubule and projects into the internal region of the distal section of the plastic tubule, whereby the support element is attached to the metal tubule such that an inner cavity of the metal tubule remains completely free.

16. The catheter as claimed in claim 14, characterized in that the metal tubule comprises a slit introduced into the metal tubule, which slit extends from the distal end of the metal tubule in the longitudinal direction of the metal tubule, wherein the slit is embodied for partly holding the support element, and that the support element at most extends in the distal direction to a proximal region of the at least one lateral opening.

17. The catheter as claimed in claim 13, characterized in that the proximal end of the plastic tubule is pushed onto the distal end of the metal tubule and attached to the distal end of the metal tubule by pressure welding.

18. A set of instruments, comprising a catheter as claimed in claim 1, a guide wire, and a special wire for diagnostic, surgical, and/or therapeutic purposes.

19. The set of instruments as claimed in claim 18, characterized in that an external diameter of the guide wire and an external diameter of the special wire together at most correspond approximately to the internal diameter of the lumen in the region between the distal end and the first lateral opening, whereby a diameter of the first lateral opening approximately corresponds to the external diameter of the guide wire, while the second lateral opening has a diameter that approximately corresponds to the external diameter of the special wire.

20. The set of instruments as claimed in claim 18, characterized in that the special wire is embodied as a probe wire for a tomographic method, wherein this is a probe wire for optical coherence tomography.

\* \* \* \* \*